(12) United States Patent
Yoda

(10) Patent No.: US 10,426,352 B2
(45) Date of Patent: Oct. 1, 2019

(54) OBJECT INFORMATION ACQUIRING APPARATUS, INFORMATION PROCESSING APPARATUS AND OBJECT INFORMATION ACQUIRING METHOD

(71) Applicant: CANON KABUSHIKI KAISHA, Tokyo (JP)

(72) Inventor: Haruo Yoda, Nishitama-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1542 days.

(21) Appl. No.: 13/957,779

(22) Filed: Aug. 2, 2013

(65) Prior Publication Data

US 2014/0058262 A1    Feb. 27, 2014

(30) Foreign Application Priority Data

Aug. 23, 2012 (JP) .................. 2012-183971

(51) Int. Cl.
*A61B 5/00* (2006.01)
*G01S 15/89* (2006.01)
(Continued)

(52) U.S. Cl.
CPC ............. *A61B 5/0095* (2013.01); *A61B 8/44* (2013.01); *G01S 7/52047* (2013.01);
(Continued)

(58) Field of Classification Search
CPC .......... A61B 8/00; A61B 8/44; A61B 5/0095; A61B 8/483; G10K 11/346; G01S 15/8915; G01S 15/8945; G01S 7/52047
See application file for complete search history.

(56) References Cited

U.S. PATENT DOCUMENTS 5,349,524 A * 9/1994 Daft ................. G01S 15/8981
367/135
6,594,367 B1 * 7/2003 Marash ............... G10K 11/341
367/119
(Continued)

FOREIGN PATENT DOCUMENTS

CN    A 1714752    1/2006
CN    A 102341723    2/2012
(Continued)

OTHER PUBLICATIONS

M Li and G Hayward, Ultrasound Nondestructive Evaluation (NDE) Imaging with Transducer Arrays and Adaptive Processing, Sensors, 2012, www.mdpi.com/journal/sensors, vol. 12, pp. 42-54.*
(Continued)

*Primary Examiner* — James M Kish
(74) *Attorney, Agent, or Firm* — Venable LLP

(57) ABSTRACT

An object information acquiring apparatus is provided that includes: a plurality of receiving elements which receive an acoustic wave that propagates from an object, and which convert the acoustic wave to a reception signal; an adaptive beamformer that performs adaptive beamforming of adjusting reception directionality in accordance with the reception signal in use of the reception signal; a delay-and-sum beamformer that performs delay-and-sum beamforming having preset directionality in use of the reception signal; an amplitude modulator that uses one output signal of one of the adaptive beamformer and the delay-and-sum beamformer, to perform amplitude modulation on an output signal of the other one of the beamformers; and a generator that, on the basis of a signal outputted by the amplitude modulator, generates image data on the interior of the object.

33 Claims, 9 Drawing Sheets

(51) Int. Cl.
*G01S 7/52* (2006.01)
*G10K 11/34* (2006.01)
*A61B 8/00* (2006.01)
*A61B 8/08* (2006.01)

(52) U.S. Cl.
CPC ...... *G01S 15/8915* (2013.01); *G01S 15/8945* (2013.01); *G10K 11/346* (2013.01); *A61B 8/483* (2013.01)

(56) References Cited

U.S. PATENT DOCUMENTS

| | | | |
|---|---|---|---|
| 6,798,380 B2 | 9/2004 | Li et al. ................... 342/368 |
| 7,740,583 B2 | 6/2010 | Rigby et al. ................... 600/437 |
| 2003/0065262 A1 | 4/2003 | Stergiopoulos et al. ..... 600/347 |
| 2003/0158482 A1* | 8/2003 | Poland ................ G01H 1/00 600/446 |
| 2003/0231125 A1* | 12/2003 | Freeman ............ G01S 7/52028 341/143 |
| 2005/0081636 A1* | 4/2005 | Barshinger .......... G01N 29/262 73/606 |
| 2009/0198127 A1* | 8/2009 | Li ......................... A61B 5/015 600/437 |
| 2011/0128816 A1 | 6/2011 | Baba et al. ................... 367/11 |
| 2011/0307181 A1 | 12/2011 | Nagae ........................... 702/19 |
| 2012/0020480 A1* | 1/2012 | Visser ...................... H04R 3/12 381/17 |
| 2012/0022373 A1 | 1/2012 | Tateyama ................... 600/437 |
| 2012/0044785 A1 | 2/2012 | Yoda et al. ................... 367/22 |
| 2012/0281902 A1 | 11/2012 | Oikawa et al. .............. 382/131 |
| 2012/0314534 A1 | 12/2012 | Yoda et al. ................... 367/7 |
| 2013/0308850 A1 | 11/2013 | Oikawa et al. .............. 382/131 |
| 2013/0338501 A1* | 12/2013 | Clingman ........... A61B 5/0035 600/440 |

FOREIGN PATENT DOCUMENTS

| | | |
|---|---|---|
| CN | A 102449499 | 5/2012 |
| JP | 2006-271291 | 10/2006 |
| JP | 2010-200926 | 9/2010 |
| JP | 2012-080994 | 4/2012 |
| JP | A 2010-200926 | 9/2012 |
| JP | 2012-223430 | 11/2012 |
| WO | WO 2010/100868 | 9/2010 |
| WO | WO 2011057252 A1 * | 5/2011 ......... G01S 7/52047 |
| WO | WO 2012/035723 | 3/2012 |

OTHER PUBLICATIONS

Office Action dated Nov. 19, 2014 in counterpart Chinese (P.R.C.) patent application 201310362923.7, with translation.

J.-F. Synnevåg et al., "Adaptive Beamforming Applied to Medical Ultrasound Imaging", *IEEE Trans. Ultrasonics, Ferroelectrics, And Frequency Control*, vol. 54, No. 8, pp. 1606-1613 (Aug. 2007).

B. Asl et al., "Minimum Variance Beamforming Combined with Adaptive Coherence Weighting Applied to Medical Ultrasound Imaging", *IEEE Transactions on Ultrasonics, Ferroelectrics, and Frequency Control*, vol. 56, No. 9, pp. 1923-1931 (Sep. 2009).

EESR issued Nov. 20, 2013 in counterpart European Patent Application 13180189.6.

\* cited by examiner

OBJECT INFORMATION ACQUIRING APPARATUS, INFORMATION PROCESSING APPARATUS AND OBJECT INFORMATION ACQUIRING METHOD

BACKGROUND OF THE INVENTION

Field of the Invention

The present invention relates to an object information acquiring apparatus, an information processing apparatus and an object information acquiring method.

Description of the Related Art

Ultrasound imaging devices for imaging of three-dimensional structures in the interior of an object, using ultrasound waves, are widely used as ultrasound diagnosis devices in the medical field.

The performance of ultrasound diagnosis devices improves rapidly year by year in the wake of advances in ultrasound imaging technology. Image reconstruction relying on adaptive signal processing is being researched as one technology aimed at further enhancing that performance. For instance, J. F. Synnevag, et al., "Adaptive Beamforming Applied to Medical Ultrasound Imaging", IEEE Trans. ULTRASONIC, FERROELECTRICS, AND FREQUENCY CONTROL, VOL. 54, NO. 8, AUGUST 2007, reports an ultrasound wave beamforming technology that relies on adaptive signal processing in the form of a DCMP (Directionally Constrained Minimization of Power) method.

The DCMP method is an adaptive signal processing technology developed as one technology in adaptive antennas. The DCMP method is a reception method that involves adaptively adjusting reception directionality on the basis of a constraint condition, namely rendering constant the reception gain of arriving waves in a desired direction, and minimizing the intensity of all reception signals including interfering waves. This method allows minimizing the ratio of interfering wave intensity with respect to signal intensity, and hence allows receiving signals having good SN ratio. As is likewise known, this method allows improving resolution and contrast in reconstructed images as compared with ordinary beamforming methods that are based on delay-and-sum. The DCMP method is also referred to as the CAPON method.

The specification of US Patent Application Publication No. 2003/0065262 (Patent Literature 2) and the specification of U.S. Pat. No. 6,798,380 (Patent Literature 3) disclose calculation methods in instances where the DCMP method is used in ultrasound imaging. Japanese Patent Application Laid-Open No. 2010-200926 (Patent Literature 1) discloses a beam signal synthesis method in which an output signal from beamforming based on the DCMP method and an output signal from delay-and-sum beamforming are compared, and the smaller signal is outputted.

Patent Literature 1: Japanese Patent Application Laid-Open No. 2010-200926
Patent Literature 2: Specification of US Patent Application Publication No. 2003/0065262
Patent Literature 3: Specification of U.S. Pat. No. 6,798,380
Non Patent Literature 1: J. F. Synnevag, et al., "Adaptive Beamforming Applied to Medical Ultrasound Imaging", IEEE Trans. ULTRASONIC, FERROELECTRICS, AND FREQUENCY CONTROL, VOL. 54, NO. 8, AUGUST 2007

SUMMARY OF THE INVENTION

Ultrasound wave beamforming by the DCMP method is advantageous in that this method affords significantly enhanced resolution in reconstructed images. As is known, however, the DCMP method is problematic in that signal components from a focus point are cancelled when correlated interference waves, which are correlated with the signal component arriving from the focus point, are inputted as noise. In the case of ultrasound imaging, one transmission wave is reflected in various reflecting bodies, and composite signals thereof are received. In principle, therefore, noise waves from points other than the focus point are all correlated interference waves, which poses a particularly serious problem.

Numerous additional processing operations are ordinarily required in order to solve the above problem, for instance a spatial averaging processing of a correlation matrix, a temporal averaging processing of a correlation matrix, and/or summation of small positive numbers to the diagonal terms of a correlation matrix, in a case where the DCMP method is used in ultrasound images. These additional processing operations mitigate the problems of the DCMP method, and are effective in enhancing the robustness of beamforming for reception signals that include various noise waves.

However, these additional processing operations detract somewhat from the characteristics of the DCMP method, and thus the characteristics of the DCMP method were in some instances inferior, depending on the above conditions, to those of an ordinary delay-and-sum beamforming method. Specifically, circumstances arose readily where the DCMP method was superior in terms of resolution, but the delay-and-sum method was superior in terms of contrast. That is, resolution is good but contrast is unsatisfactory the DCMP method, whereas contrast is good but resolution unsatisfactory in delay-and-sum beamforming.

Accordingly, some novel output signal generation means is required that combines the output signals of two or more beamforming methods having thus dissimilar advantages and shortcomings, and that emphasizes the advantages of the methods.

In the light of the above, it is an object of the present invention to provide a device that generates image data on the interior of an object by performing adaptive signal processing on ultrasound waves that are received from the object, and to enhance image quality.

The present invention provides an object information acquiring apparatus, comprising:

a plurality of receiving elements configured to receive an acoustic wave that propagates from an object, and configured to convert the acoustic wave to a reception signal that is an electric signal;

an adaptive beamformer configured to perform adaptive beamforming of adjusting reception directionality in accordance with the reception signal in use of the reception signal;

a delay-and-sum beamformer configured to perform delay-and-sum beamforming having preset directionality in use of the reception signal;

an amplitude modulator configured to use an output signal of one of the adaptive beamformer and the delay-and-sum beamformer, to perform amplitude modulation on an output signal of the other one of the beamformers; and a generator configured to, on the basis of a signal outputted by the amplitude modulator, generate image data on the interior of the object.

The present invention also provides an information processing apparatus that generates image data on the interior of an object on the basis of a reception signal that is outputted by a plurality of receiving elements that receive an acoustic wave that propagates from the object, the information processing apparatus comprising:

an adaptive beamformer configured to perform adaptive beamforming of adjusting reception directionality in accordance with the reception signal in use of the reception signal;

a delay-and-sum beamformer configured to perform delay-and-sum beamforming having preset directionality in use of the reception signal; and an amplitude modulator configured to use an output signal of one of the adaptive beamformer and the delay-and-sum beamformer, in order to perform amplitude modulation on an output signal of the other one of the beamformers.

The present invention also provides an object information acquiring method, comprising:

a step of receiving, by a plurality of receiving elements, an acoustic wave that propagates from an object, and converting the acoustic wave to a reception signal that is an electric signal;

an adaptive beamforming step of performing adaptive beamforming of adjusting reception directionality in accordance with the reception signal in use of the reception signal;

a delay-and-sum beamforming step of performing delay-and-sum beamforming having preset directionality in use of the reception signal;

an amplitude modulation step of performing amplitude modulation in use of an output signal in one of the adaptive beamforming step and the delay-and-sum beamforming step, in order to perform amplitude modulation on an output signal of the other; and a generation step of, on the basis the amplitude-modulated signal, generating image data on the interior of the object.

The present invention succeeds in providing a device that generates image data on the interior of an object by performing adaptive signal processing on ultrasound waves that are received from the object, and succeeds in enhancing image quality.

Further features of the present invention will become apparent from the following description of exemplary embodiments with reference to the attached drawings.

DESCRIPTION OF THE EMBODIMENTS

Figure 1:
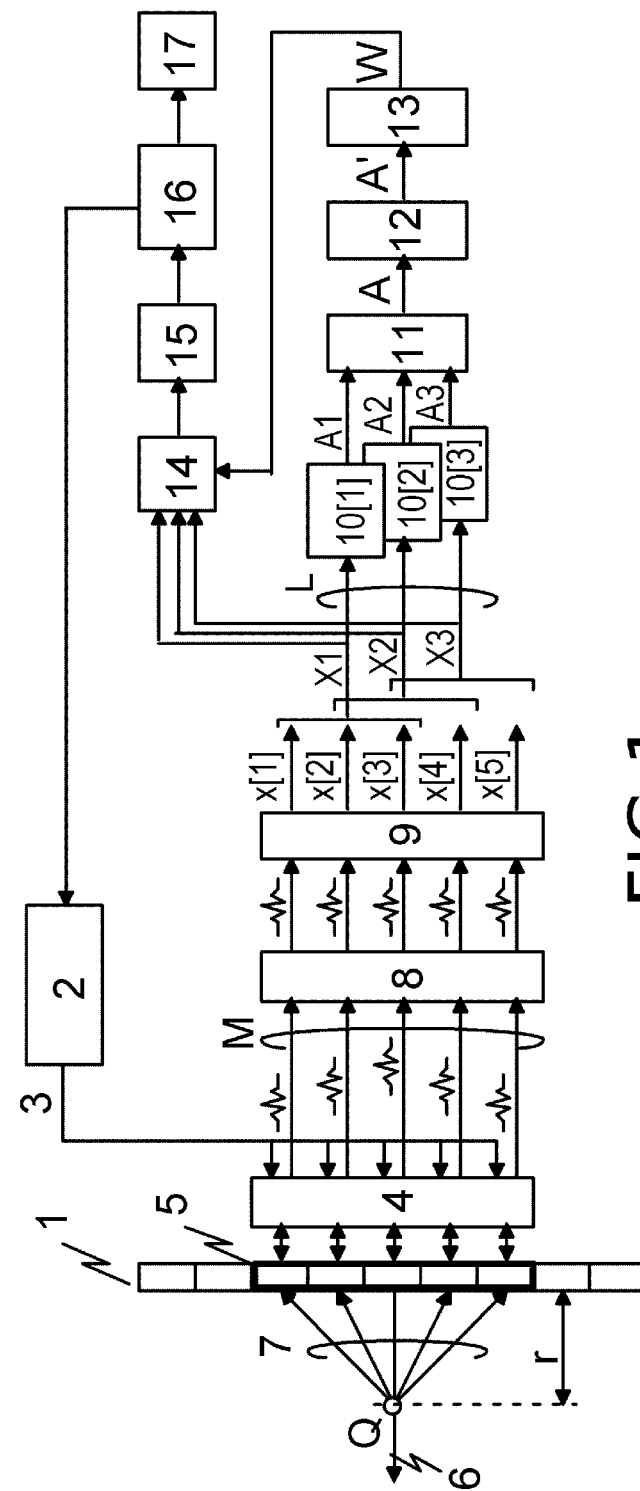
FIG. 1 is a diagram illustrating the configuration of a conventional device that utilizes a DCMP method.
Figure 2A:
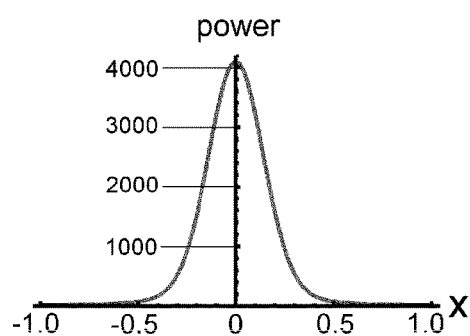
FIGS. 2A to 2D are diagrams illustrating examples of line waveforms by a delay-and-sum method and a DCMP method.
Figure 2B:
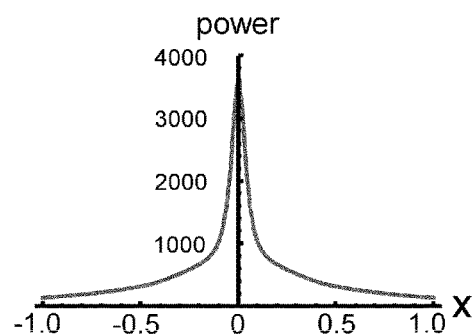
Figure 2C:
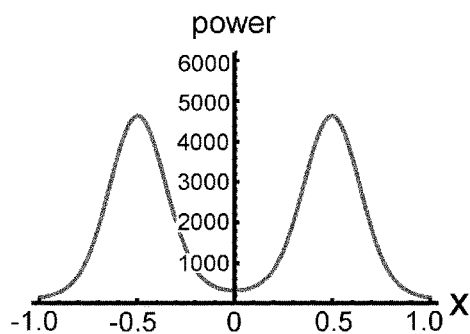
Figure 2D:
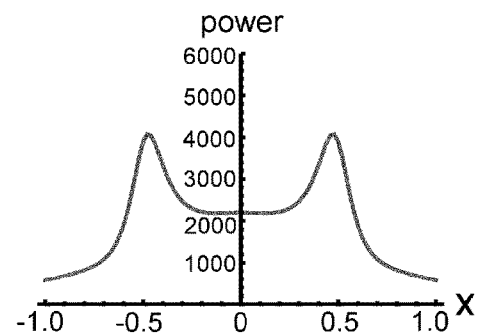

Embodiments of the present invention are explained in detail below with reference to accompanying drawings. The specific computational expressions, calculation procedures and so forth described below are to be modified, as appropriate, in accordance with the configuration of the device in which the invention is to be used, and depending on various conditions. The scope of the invention is thus not limited to the features set forth below.

The object information acquiring apparatus of the present invention encompasses an ultrasound imaging method and apparatus that rely on an ultrasound wave echo technology that involves transmitting ultrasound waves to an object, receiving reflected waves (echo waves) that are reflected in, and that propagate through, the interior of the object, and acquiring object information in the form of image data. The invention encompasses also a photoacoustic imaging method and apparatus in which light (electromagnetic waves) is irradiated onto an object, and acoustic waves that are thereupon generated in and that propagate through the object, on account of the photoacoustic effect, are received, and object information is acquired in the form of image data.

In the case of a device that relies on the former ultrasound wave echo technology, the object information that is acquired is information that reflects differences in the acoustic impedance among tissues in the object interior. In the case of the latter device that relies on the photoacoustic effect, the object information that is acquired denotes the distribution of sources of acoustic waves that are generated as a result of light irradiation, the initial sound pressure distribution inside the object, or the light energy absorption density distribution and/or absorption coefficient distribution derived from the initial sound pressure distribution, as well as the distribution of the concentration of substances that make up the tissues. The substance concentration distribution may be, for instance, an oxygen saturation distribution, an oxyhemoglobin-reduced hemoglobin concentration distribution or the like.

As used in the present invention, the term acoustic wave encompasses elastic waves referred to as sound waves, ultrasound waves and acoustic waves, typically ultrasound waves. Acoustic waves generated on account of the photoacoustic effect are referred to as photoacoustic waves or photo-ultrasound waves. An acoustic detector (for instance, a probe) receives acoustic waves that are generated or reflected in the object and that propagate through the latter.

The present invention can also be regarded as an object information acquiring method for realizing, through control by a computer or the like, the various operations that are performed in the object information acquiring apparatus. In a case where electric signals resulting from conversion of acoustic waves already acquired by a probe are stored in a storage device, the present invention can also be regarded as an information processing apparatus in which these signals are used to construct object information in the form of image data.

In the disclosure below, the term delay-and-sum denotes processing of working out object information taking into consideration the positions of a plurality of receiving elements in an ultrasound wave probe, as well as target positions inside the object. More specifically, there is carried out delaying processing for a plurality of reception signals in accordance with the direction in which the acoustic waves are transmitted and in accordance with the return positions of the waves (positions at which acoustic waves are generated, in cases where the photoacoustic effect resorted to). Summation processing is then performed on the plurality of reception signals after the delaying processing. That is, delay-and-sum processing is executed herein. Such delay-and-sum processing is processing, based on reception beamforming, of generating signals corresponding to the sound pressure of acoustic waves from respective positions inside the object.

Summation in the delay-and-sum processing may be performed after multiplication of the plurality of reception signals by respective weights. Specifically, the observation position and the conditions of transmission and reception are known before signal reception, and hence a good image can be obtained by performing the summation processing by multiplying the reception signals by weights that are established in accordance with these conditions. A method that utilizes, as such weights, fixed weights that are calculated beforehand in accordance with the observation position and the transmission and reception conditions may be referred to as fixed-type signal processing that is performed in ordinary delay-and-sum processing operations.

Other methods that can be carried out include methods in which the weights used for multiplication vary adaptively in accordance with the reception signals, i.e. adaptive signal processing methods. Examples thereof include, for instance, the above-described DCMP method (CAPON method). In such adaptive beamforming, reception directionality is adjusted in accordance with reception signals.

Processing of signal intensities (volume data) thus obtained at each position (pixel or voxel) inside the object is also referred to as image reconstruction, in the meaning of construction of image data for display.

An example of a conventional DCMP method will be explained before the present invention is explained in detail.

FIG. 1 illustrates the configuration of a conventional object information acquiring apparatus that relies on a DCMP method. In the figure, a transmission signal control circuit 2 generates a transmission signal 3, according to an instruction from a CPU 16, drives ultrasound wave transmitting and receiving element group 5 of an ultrasound wave probe 1 via a transmission and reception control circuit 4, and transmits a pulsed ultrasound wave beam 6.

An ultrasound echo wave 7 generated through reflection of the ultrasound wave beam 6 is converted once more to electric signals of M channels by the ultrasound wave transmitting and receiving element group 5, and is sent to a phasing delay circuit 8 via the transmission and reception control circuit 4. The sent electric signals are converted to digital signals by an AD conversion circuit (not shown). The phasing delay circuit 8 adjusts the delay time of the signals in such a manner that the arrival times of an echo signal from an arbitrary point Q on the ultrasound wave beam 6 are equalized.

A complex transform circuit 9 converts M-channel signals, the delay times whereof have been adjusted, to respective complex signals. The complex transform processing in the complex transform circuit 9 involves generating signals in which the phase of each frequency component is shifted by 90°, on the basis of input signals comprising a real value sequence, and adding the 90° phase-shifted signals as the imaginary parts, to convert thereby the signals to complex signals. The 90° phase-shifted signals can be calculated using a FIR filter with odd taps and odd-symmetry coefficients, and hence the complex transform circuit 9 can be realized easily. The M channel output signals at a point in time t in the complex transform circuit 9 are notated as x[1,t], x[2,t], x[3,t], . . . , x[M,t] in the explanation below. In the figure, M corresponds to 5, and the point in time t is omitted.

The procedure for calculating a complex correlation matrix A[t] out of the complex reception signals x[1,t], x[2,t], x[3,t], . . . , x[M,t] obeys a known spatial averaging method as a method for attenuating the influence of correlated interference waves. In a spatial averaging method, sub-array signal vectors Xj[t] are defined by taking M complex signals in L batches, as in Expression (1), and a complex correlation matrix is calculated according to Expression (2). Ordinarily, a numerical value of about M/2 is used as the numerical value L. In Expression (2), the symbol H in the superscript of Xj[t] denotes the transpose and complex conjugate of a vector.

[Math 1]

$$Xj[t] = \begin{pmatrix} x[j, t] \\ x[j+1, t] \\ \vdots \\ x[j+L-1, t] \end{pmatrix}, \quad (1)$$

$$j = 1, 2, \ldots, M - L + 1$$

$$A[t] = \frac{1}{M - L + 1} \cdot \sum_{j=1}^{M-L+1} Xj[t]Xj[t]^H \quad (2)$$

In the figure, correlation matrix calculation circuits 10[1], 10[2], 10[3] are circuits that calculate respective correlation matrices of sub-array signal vectors X1[t], X2[t], X3[t]. An averaging circuit 11 summates and averages the calculated correlation matrices, and outputs the complex correlation matrix A[t] of Expression (2). In the figure, L corresponds to 3.

A correlation matrix modifying circuit 12 is a calculation circuit that summates ε×Trace[A], which is proportional to Trace[A], to the diagonal terms of the complex correlation matrix A[t], to yield a modified complex correlation matrix A'[t]. Herein, ε is a small positive number, and Trace[A] is the sum of the diagonal terms of matrix A. The processing of summating ε×Trace[A] to the diagonal terms elicits the effect of stabilizing a subsequent optimal weight calculation and of enhancing the robustness of the output by the DCMP method. In the computational expression, as given by Expression (3), I denotes a unit matrix.

[Math 2]

$$A'[t] = A[t] + \varepsilon \cdot \text{Trace}[A[t]] \cdot I \quad (3)$$

Although not depicted in the example of the figure, the complex correlation matrix A[t] may similarly be temporally averaged in order to enhance the robustness of the output by the DCMP method.

A weight vector calculation circuit 13 calculates an optimal weight vector W[t] using the modified complex correlation matrix A'[t] and a known constraint vector C. According to the DCMP method, the optimal weight vector W[t] is given as a vector W[t] that minimizes a signal intensity P of Expression (5) under the constraint condition of Expression (4).

[Math 3]

$$W[t]^H C = 1 \quad (4)$$

$$P[t] = W[t]^H A' W[t] \quad (5)$$

The problem of working out the optimal weight vector W that minimizes P, with Expression (4) as the constraint condition, can be solved analytically. The solution of the optimal weight vector W[t] is given by Expression (6). The superscript −1 of A'[t] denotes an i matrix of A'[t]. The constraint vector C is a known vector that designates the arrival direction of the signals to be received, such that ordinarily all the elements of the vector are set to 1 for the phasing delay output signal. For convenience in the explanation below, the constraint vector used herein has the magnitude thereof normalized to 1, as in Expression (7). The weight vector calculation circuit 13 calculates Expression (6).

[Math 4]

$$W[t] = \frac{A'[t]^{-1}C}{C^H A'[t]^{-1}C} \quad (6)$$

$$C = \frac{1}{\sqrt{L}} \cdot \begin{pmatrix} 1 \\ 1 \\ \vdots \\ 1 \end{pmatrix} \quad (7)$$

An output signal calculation circuit 14 calculates a complex output signal Y(t) according to Expression (8), on the basis of the optimal weight vector W[t] and sub-array complex signal vectors Xj[t]. A signal intensity calculation circuit 15 calculates an output signal intensity Pow[t] according to Expression (9), on the basis of the output signal Y, and forwards the result to the CPU 16.

[Math 5]

$$Y[t] = \sum_{j=1}^{M-L+1} Xj[t]^H W[t] \quad (8)$$

$$Pow[k] = |Y[t]|^2 \quad (9)$$

The CPU 16 can obtain thereby high-precision echo intensity signals on the transmission beam path. By way of the transmission signal control circuit 2, the CPU 16 causes the transmission position and direction of an ultrasound wave beam to be sequentially scanned, gathers the echo intensity signals on the respective ultrasound wave beam paths, and, on the basis thereof, creates an echo image and displays the echo image on a display device 17.

The processing operations from Expression (1) to Expression (9) can be calculated using a digital circuit means or a general-purpose high-speed computer. Accordingly, an object information acquiring apparatus that relies on the DCMP method can be realized by executing the above procedure.

An example has been explained in detail of an instance where a conventional DCMP method is applied to ultrasound wave beamforming. As is known, the echo image that is generated in accordance with the DCMP method varies substantially depending, for instance, on the small parameter ε that is given by Expression (3). If the small parameter ε was set to be very small, the resolution of isolated point targets present inside the object was significantly enhanced; in some instances, however, the signal intensity was significantly reduced in the case of linear targets or the like, on account of interference with reflected waves from the surroundings.

As the small parameter ε increases, the echo image asymptotically approaches a delay-and-sum echo image of sub-array reception signals. The signal number L of the sub-array reception signals is narrowed to about half the original reception signal number M. Therefore, this means that setting a large small parameter ε results in an asymptotic approach to a delay-and-sum image of poorer resolution than that of an ordinary delay-and-sum image from M element signals.

These problems can be avoided to some extent by appropriately selecting the value of the ε parameter. Even upon appropriate selection of the value of the ε parameter, however, a possibility remained of decreased image contrast, compared to that of an ordinary delay-and-sum method, depending on the way in which reflecting bodies were distributed inside the object.

Methods wherein a correlation matrix is temporally smoothed and is used for optimal weight calculation constitute likewise an effective method for improving the robustness of the DCMP method. In some instances, however, such a method as well gave rise to decreased image contrast, depending on the conditions. As is characteristic of the DCMP method, resolution and image contrast decreased in some instances, similarly to cases where ε was set to a large value, when substantial reception random noise was superposed on the reception signal.

FIG. 2 illustrates one-line waveforms of an output echo image by the delay-and-sum method and the DCMP method, under given conditions. FIG. 2A illustrates results of delay-and-sum of an isolated point target, FIG. 2B illustrates results by the DCMP method, FIG. 2C illustrates results of delay-and-sum of two separated point targets, and FIG. 2D illustrates results by the DCMP method. The results show that peak width in the echo image by the DCMP method is narrower than that by the delay-and-sum method, and thus the former is superior in terms of resolution. However, the echo image by the DCMP method exhibits higher signal level at sites spaced apart from the peaks, which indicates that the method is inferior in terms of contrast.

In view of the above, there is a need for combining the outputs of the two beamforming methods having dissimilar characteristics, to generate a new output signal that brings out the advantages of both methods. In other words, it is necessary to enhance image quality in devices that generate image data on the interior of an object by subjecting ultrasound waves received from the object to adaptive signal processing (DCMP method).

Example 1

Figure 3:
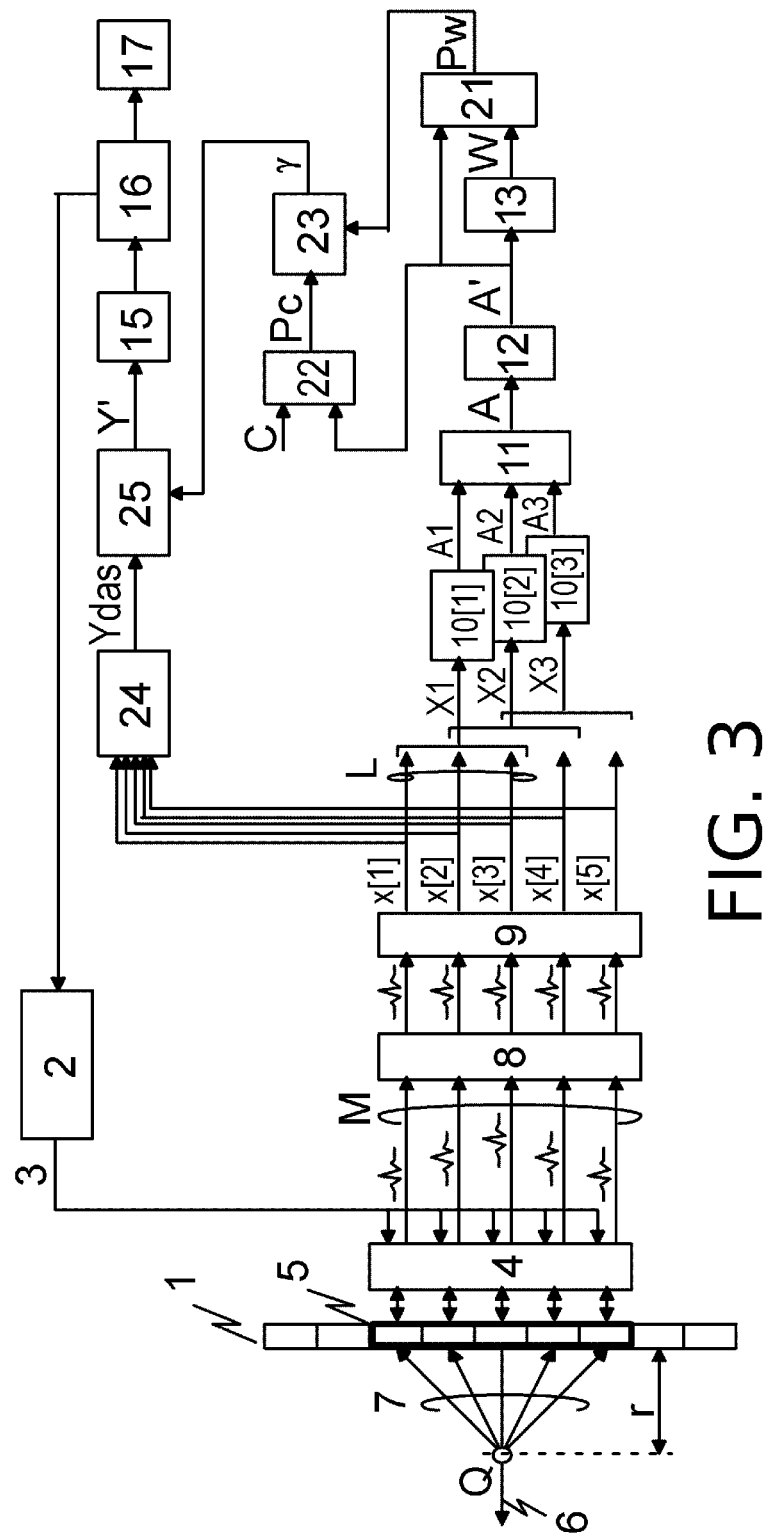
FIG. 3 is a diagram illustrating the configuration of a device according to Example 1.

FIG. 3 is a diagram illustrating a device according to Example 1. Compared with the conventional example of FIG. 1, herein blocks 21 to 25 have been added in Example 1 in place of the output signal calculation circuit 14. The explanation below will focus on this difference.

A signal intensity calculation circuit 21 calculates, on the basis of Expression (10), an output signal intensity Pw according to the DCMP method, from the modified correlation matrix A'[t] and the optimal weight vector W[t].

[Math 6]

$$Pw[t] = W[t]^H A'[t] W[t] \quad (10)$$

A signal intensity calculation circuit 22 calculates, on the basis of Expression (11) a signal intensity Pc in the direction of arrival of the signals to be received, from the modified correlation matrix A'[t] and the constraint vector C.

[Math 7]

$$Pc[t] = C^H A'[t] C \quad (11)$$

Herein, A'[t] can be approximated by A[t] if the ε parameter is a small positive number, and hence the signal intensity Pc is substantially equal to the average signal intensity from delay-and-sum of sub-array signals as given by Expression (12). Therefore, the calculation of Pc in Expression (11) can be performed directly on the basis of the average signal intensity from delay-and-sum of the sub-array signals Xj.

[Math 8]

$$Pc[t] \cong C^H A[t]C \qquad (12)$$
$$= \frac{1}{M-L+1} \cdot C^H \left( \sum_{j=1}^{M-L+1} Xj[t]Xj[t]^H \right) C$$
$$= \frac{1}{M-L+1} \cdot \sum_{j=1}^{M-L+1} |Xj[t]^H C|^2$$

A modulation ratio calculation circuit 23 calculates a ratio between the two output signal intensities Pw and Pc, to calculate thereby a modulation ratio γ, as in Expression (13).

[Math 9]

$$\gamma[t] = \frac{Pw[t]}{Pc[t]} = \frac{W[t]^H A'[t]W[t]}{C^H A'[t]C} \qquad (13)$$

The numerator Pw[t] in Expression (13) is the minimum intensity calculated on the basis of the constraint condition of Expression (4). When the constraint vector C is considered as one weight vector, the constraint vector C is also a weight vector that satisfies the constraint condition of Expression (4). As a result, this ensures that the modulation ratio γ calculated according to Expression (13) holds within the range of Expression (14).

[Math 10]

$$0 \leq \gamma[t] \leq 1 \qquad (14)$$

A summating circuit 24 summates the input signals, and calculates a beamforming signal Ydas based on a delay-and-sum method. The calculated delay-and-sum signal Ydas is subjected to amplitude modulation in an amplitude modulation circuit 25, as in Expression (15), and the modulated delay-and-sum signal Y'[t] is sent to the signal intensity calculation circuit 15.

[Math 11]

$$Y'[t]=Ydas[t]\cdot\gamma[t] \qquad (15)$$

The signal intensity calculation circuit 15 performs envelope detection and conversion to intensity signals on the delay-and-sum signal Y'[t], and forwards the result to the CPU 16. The CPU 16 receives the input of the intensity signals for each ultrasound wave beam, reconstructs the signals to an echo image, and displays the result on the display circuit 17.

Thus, the processing from Expression (10) to Expression (15) can be calculated using a digital circuit means or a general-purpose high-speed computer, and hence the present invention can be realized in an easy manner.

FIG. 4 is a diagram for explaining the effect of the present example, using line waveforms of an echo image for an isolated point target. FIG. 4A is an output line waveform of an ordinary delay-and-sum method corresponding to Ydas, and FIG. 4B is an output line waveform of a delay-and-sum method of sub-array signals corresponding to Pc. The waveform (FIG. 4B) of delay-and-sum of sub-array signals has fewer reception signals to be summated than in the case of a waveform (FIG. 4A) resulting from ordinary delay-and-sum, and hence the spread of the waveform is large and resolution is poor.

Figure 4A:
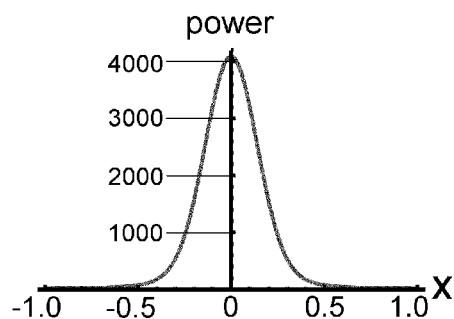
FIGS. 4A to 4E are diagrams for explaining the results in Example 1 using an echo image of a one-point target.
Figure 4B:
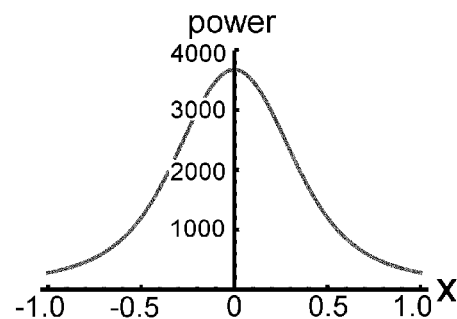
Figure 4C:
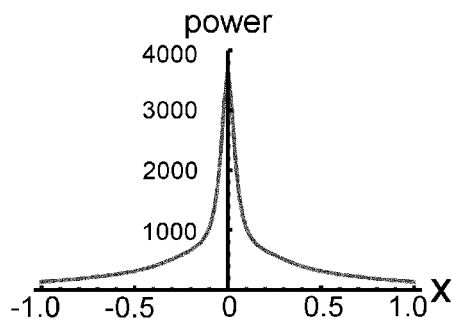
Figure 4D:
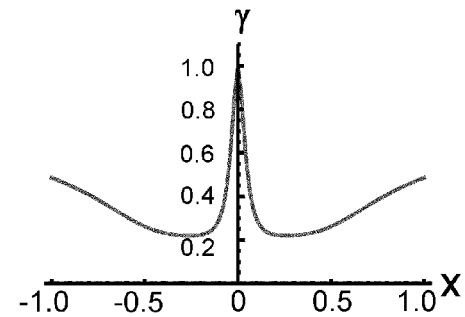

FIG. 4C is an output signal intensity waveform by the DCMP method corresponding to Pw. A comparison of the output signal intensity by the DCMP method (FIG. 4C) versus the result of delay-and-sum (FIG. 4A) reveals that although resolution improves significantly, the spread of the foot of the waveform is larger, and image contrast poorer. FIG. 4D is a modulation ratio waveform corresponding to γ. The modulation ratio γ is a ratio of the attenuation of the delay-and-sum output of sub-array signals by the DCMP method, and may be regarded as a ratio of characteristic improvement by the DCMP method. In the present example, output signals from ordinary delay-and-sum are multiplied by the "improvement" ratio γ of the DCMP method, so as to improve the output characteristic of ordinary delay-and-sum.

Figure 4E:
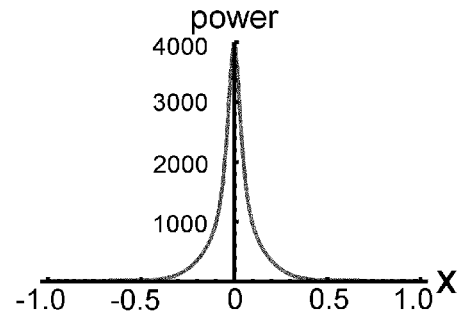
Figure 5A:
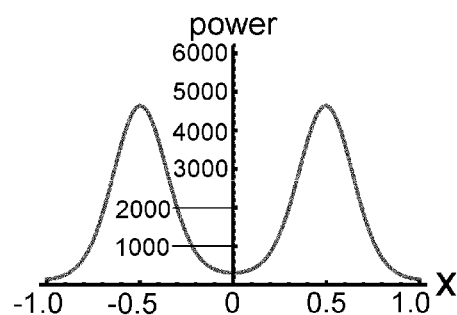
FIGS. 5A to 5E are diagrams for explaining the results in Example 1 using an echo image of a two-point target.
Figure 5B:
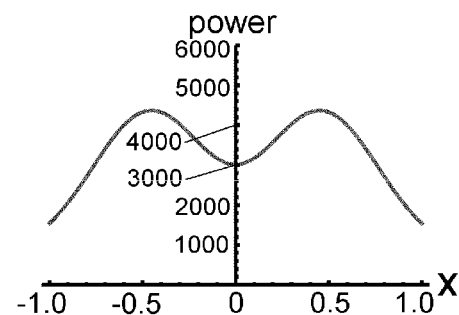
Figure 5C:
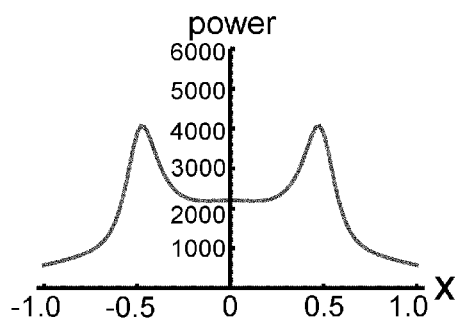
Figure 5D:
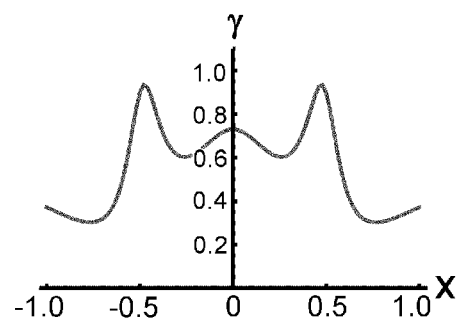
Figure 5E:
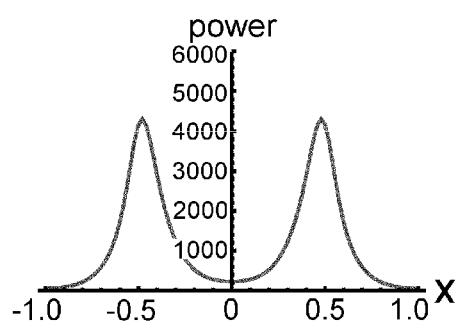

FIG. 4E is an intensity waveform of a resulting modulation output signal Y'. Through multiplication by the "improvement" ratio γ, the resulting intensity waveform of Y' (FIG. 4E) boasts the high resolution of a waveform by the DCMP method (FIG. 4C), and, at the same time, significantly attenuated foot spread, and yet better contrast than a waveform from delay-and-sum (FIG. 4A). The "improvement" ratio γ is no greater than 1, as given by Expression (14), and hence contrast can be improved beyond the result achievable by delay-and-sum.

FIG. 5 is a diagram illustrating line waveforms of echo images for two point targets. Similarly to FIG. 4, FIG. 5A is a line waveform of an echo image corresponding to Ydas, while FIG. 5B corresponds to Pc, FIG. 5C corresponds to Pw, FIG. 5D corresponds to γ, and FIG. 5E corresponds to Y'. As in the case of the isolated point target of FIG. 4, the output (FIG. 5E) in the present example is superior to both that of the delay-and-sum method and that of the DCMP method in terms of resolution and contrast.

Thus, the present invention allows combining the outputs of two beamforming methods having dissimilar characteristics, namely the delay-and-sum beamforming method and the DCMP beamforming method. In the present invention, this is equivalent to adaptive beamforming (DCMP method) being performed by an adaptive beamformer, and delay-and-sum beamforming being performed by a delay-and-sum beamformer, and is equivalent to performing amplitude modulation, by an amplitude modulator, on the output signal of one from among the adaptive beamformer and the delay-and-sum beamformer, using the output signal from the other. Image data on the interior of the object is generated on the basis of the output signal from the amplitude modulator.

As a result, it becomes possible to generate a beamforming output signal having superior characteristics. The present invention allows providing a means for realizing both high resolution and high contrast characteristics, which was hitherto not possible to achieve by resorting to a conventional single beamforming method.

Variations

The present example may accommodate various modifications in the way it is realized. The amplitude modulation processing is not limited to simple multiplication, such as the one given in Expression (15), and the modulation ratio may be corrected in an appropriate manner. For instance, a similar effect can be expected to be elicited also in a variation as in Expression (16), using an arbitrary monotonically increasing function g(x).

[Math 12]

$$Y'[t] = Ydas[t] \cdot g(\gamma[t]) \quad (16)$$

A linear interpolation formula such as the one of Expression (17) can be used as a parameter for the temporal change of α, in order to emphasize the characteristic of an ordinary delay-and-sum processing in accordance with the depth in the object interior.

[Math 13]

$$Y'[t] = Ydas[t] \cdot ((1-\alpha) + \alpha \cdot \gamma[t]) \quad (17)$$

In order to facilitate the calculation of signal intensity, delay-and-sum is performed in the present example using, as an input, the complex output of the complex transform circuit 9. However, the calculation may be realized also through summation and amplitude modulation of the real values, without modification, of the output of the phasing delay circuit 8, and through envelope detection in the signal intensity calculation circuit 15.

The calculation of Pc and Pw yields similar results even if the correlation matrix A' of Expression (10) and Expression (11) is modified to the output A of an average-calculating circuit.

Further, amplitude modulation may be carried out not on a delay-and-sum signal, as in the present example, and a similar effect can be elicited by swapping the positions of the amplitude modulation circuit 25 and the signal intensity calculation circuit 15, and by performing amplitude modulation after conversion to signal intensity.

In the calculation processing of the present invention, thus, equivalent or identical effects can be expected to be achieved by modifying the order of the various calculations, and by replacing the variables in the computational expression by similar variables. Such variations are however encompassed by the present invention, since the variations conform to the gist of latter, namely modulation of the output of one beamforming method, from among a first and a second beamforming method, using an output signal intensity of the other beamforming method.

Example 2

Figure 6:
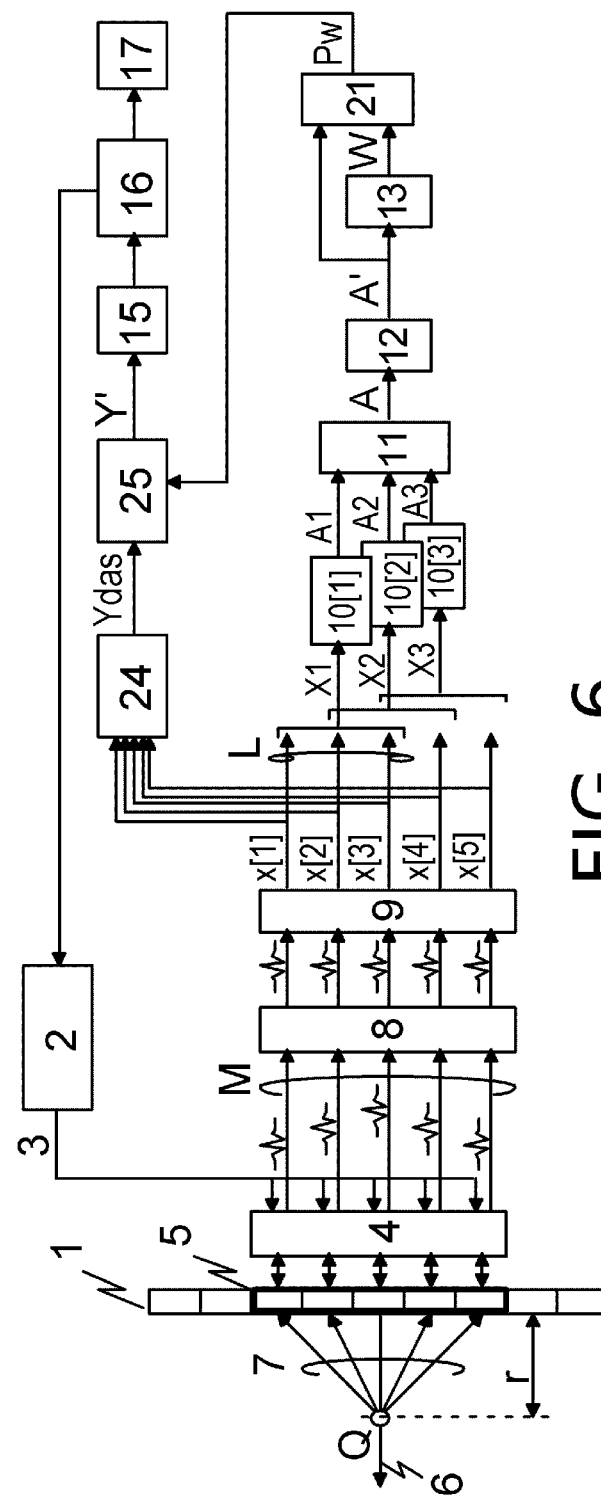
FIG. 6 is a diagram illustrating the configuration of a device according to Example 2.

FIG. 6 is a diagram illustrating a device according to Example 2. Example 2 corresponds to an example of a simplified version of Example 1. Herein, an output signal Ydas from a direct delay-and-sum beamforming method is subjected to amplitude modulation using the output signal intensity Pw from a DCMP beamforming method.

A comparison between FIG. 6 of the present example and FIG. 3 of Example 1 shows that the foregoing differ in that the signal intensity calculation circuit 22 and the modulation ratio calculation circuit 23 have been omitted, and the outputted Pw is inputted to the amplitude modulation circuit 25. That is, calculations that utilize the modulation ratio γ are not carried out.

The amplitude modulation circuit 25 in the present example may perform, for instance, the calculation processing of Expression (18a) or Expression (18b). In these mathematical expressions K is a constant. This way, an output signal that is an intermediate of the two beamforming methods can be outputted, and a composite signal can be outputted in which the shortcomings of the two beamforming methods are mitigated, though not as much as in Example 1.

[Math 14]

$$Y'[t] = Ydas[t] \cdot Pw \quad (18a)$$

$$Y'[t] = Ydas[t] \cdot \frac{Pw}{|Ydas[t]|^2 + K} \quad (18b)$$

Example 3

Figure 7:
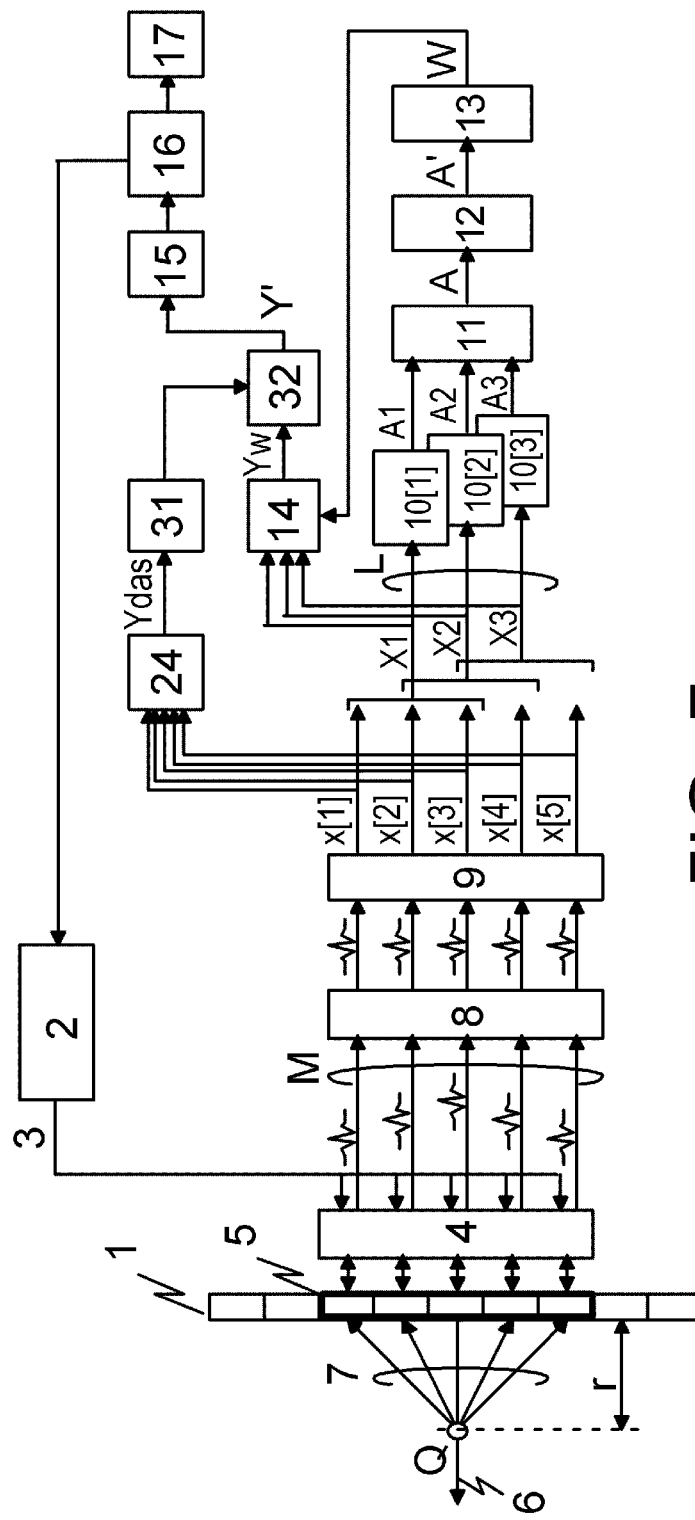
FIG. 7 is a diagram illustrating the configuration of a device according to Example 3.

FIG. 7 is a diagram illustrating a device according to Example 3. Example 3 is an example where, as opposed to Example 2, amplitude modulation of the output signal by the DCMP beamforming method is performed using an output intensity signal by the delay-and-sum beamforming method.

In the figure, the delay-and-sum signal Ydas outputted by the summating circuit 24 is converted to an intensity signal by an absolute-value circuit 31. An output signal Yw by the DCMP method, outputted by the output signal calculation circuit 14, is amplitude-modulated using the intensity signal of the delay-and-sum signal Ydas in the amplitude modulation circuit 32, and the result is inputted to the signal intensity calculation circuit 15.

For instance, the modulation output signal Y' outputted by the amplitude modulation circuit 32 is set to be as given by Expression (19a) or Expression (19b). This way, a composite signal can be outputted in which the shortcomings of the two beamforming methods are mitigated, though not as much as in Example 1.

[Math 15]

$$Y'[t] = Yw \cdot |Ydas[t]|^2 \quad (19a)$$

$$Y'[t] = Yw[t] \cdot \frac{|Ydas[t]|^2}{|Yw[t]|^2 + K} \quad (19b)$$

Example 4

Figure 8:
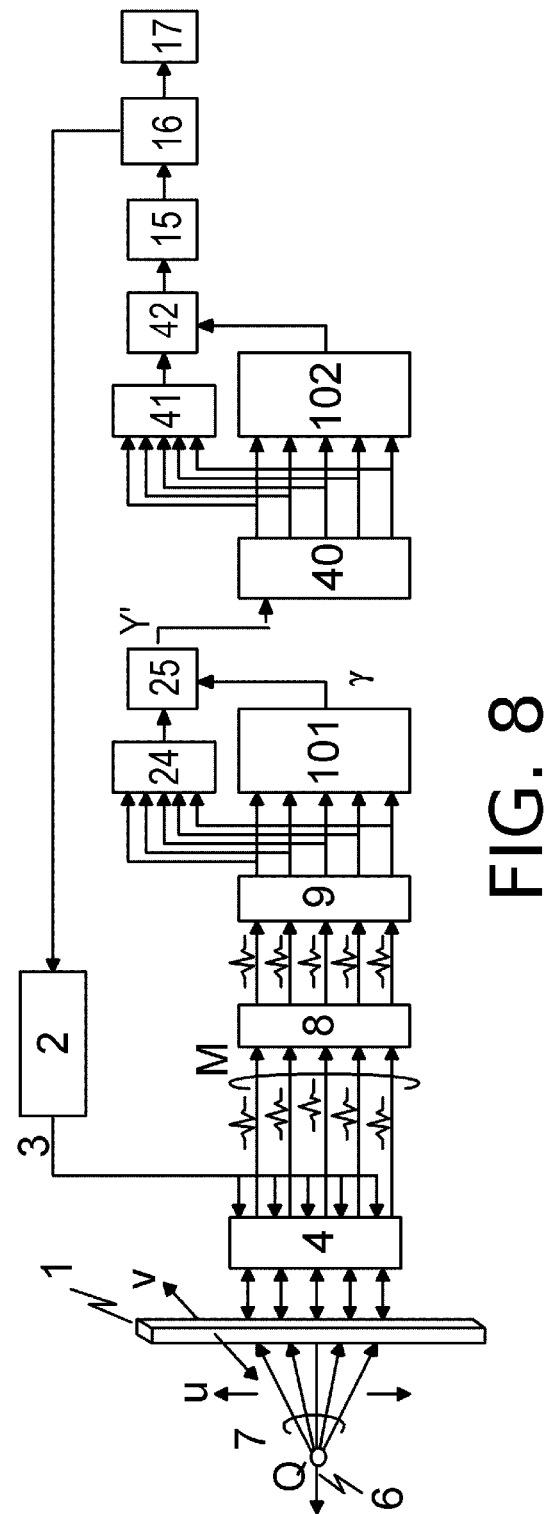
FIG. 8 is a diagram illustrating the configuration of a device according to Example 4.

FIG. 8 is an example of an instance of a device according to Example 4, where the present invention is used for two-dimensional beamforming. Two-dimensional scanning of an ultrasound wave beam in the present example is performed using the one-dimensional probe 1 in which a plurality of transmitting and receiving elements is arrayed in one dimension. Scanning in the array direction u takes place through electronic scanning by the one-dimensional probe 1, and scanning in a perpendicular direction v is accomplished through mechanical displacement of the one-dimensional probe 1.

In order to reduce ordinary calculation processing operations involved in the calculation two-dimensional beamforming, one-dimensional beamforming is performed herein in one direction, and, on the basis of the obtained result, one-dimensional beamforming is performed in a direction perpendicular to that direction. These processing operations allow acquiring image data of an object in the form of, for instance, a plurality of tomographic images, and allow displaying the internal structure of the object on a display device or the like. The direction in which the elements are arrayed and the direction of mechanical displacement are not limited to being perpendicular to each other, and it suffices that the directions intersect each other.

In the present example, a first step involves, firstly, performing electronic scanning in a u direction and mechanical scanning in a v direction, and storing the result of one-dimensional beamforming, at each scanning position in two dimensions, in a storage circuit 40. In the figure, a DCMP beamforming circuit 101 is a circuit that realizes the DCMP processing function of Example 1, and that outputs a modulation ratio γ. One-dimensional beamforming at each position can be realized in accordance with the method of Example 1, using this DCMP beamforming circuit 101 as well as the summating circuit 24 and the amplitude modulation circuit 25.

In a second step, next, the one-dimensional beamforming results, lined up in the v direction on a same u coordinate, are read parallelly from the storage circuit 40, and there is performed one-dimensional beamforming in the v direction.

A DCMP beamforming circuit 102, a summating circuit 41 and an amplitude modulation circuit 42, which are identical to the circuits denoted by the reference symbol 101, the reference symbol 24 and the reference symbol 25, perform the beamforming method of the present invention in the v direction, and the result is outputted to the intensity calculation circuit 15. The intensity calculation circuit 15 converts the output signal of the amplitude modulation circuit 42 to an output intensity signal. The CPU 16 receives the input of the output intensity signal at each position in two dimensions, from the intensity calculation circuit 15, reconstructs an echo image, and displays the echo image on the display device 17.

This way, the present invention can be easily carried out also for a two-dimensional beamforming method, and it becomes possible to provide a high-quality echo image. A combination of electronic scanning and mechanical scanning of a one-dimensional probe has been illustrated in the present example as an instance of two-dimensional scanning of an ultrasound wave beam, but it is evident that similar scanning can be carried out by electronically switching the output of a two-dimensional probe, and thus the present invention can be used in the latter case as well.

Example 5

Figure 9:
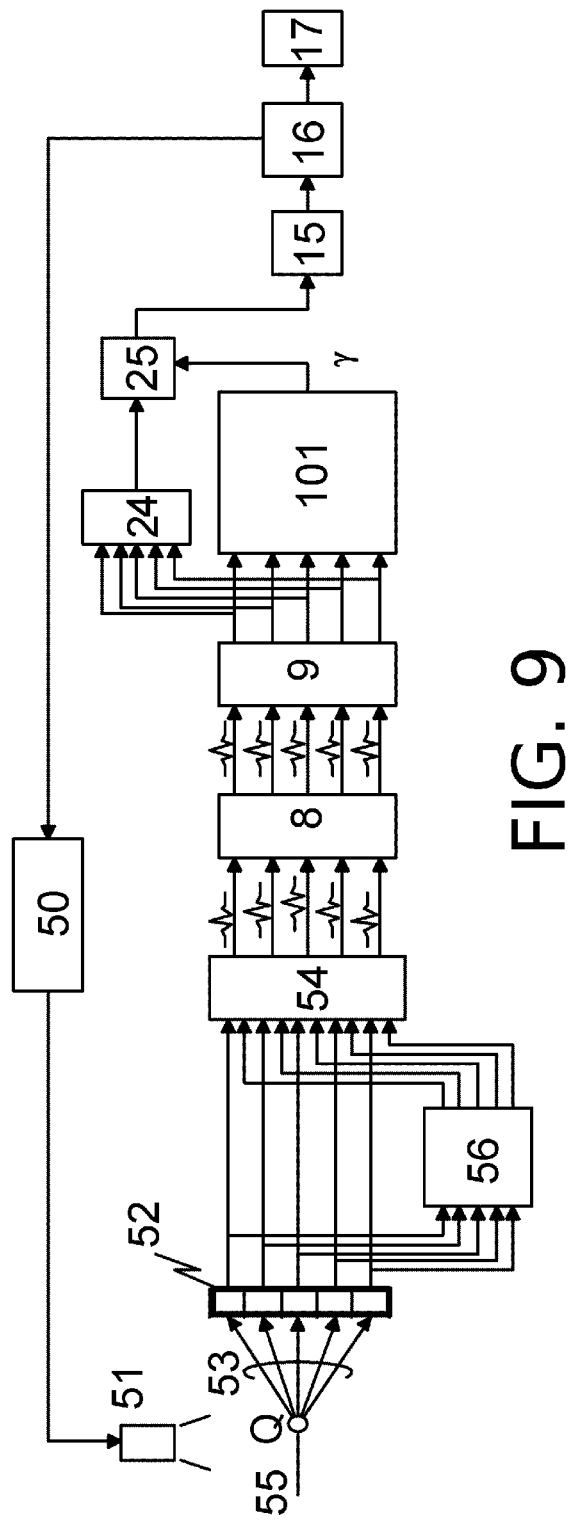
FIG. 9 is a diagram illustrating the configuration of a device according to Example 5.

FIG. 9 is an example of an instance where the present invention is used in a photoacoustic imaging device that acquires images by relying on the photoacoustic effect. In the figure, a light source 51 irradiates electromagnetic waves to the object interior via a light source control circuit 50 according to an instruction from the CPU 16. The substances to be inspected that are present in the interior of the object absorb the irradiated electromagnetic waves, and generate photoacoustic waves in unison on account of thermal expansion. An ultrasound wave receiving element group 52 converts the arriving acoustic waves to electric signals, and the signals are transmitted to the phasing delay circuit 8 by way of a selection circuit 54.

Defining herein an arbitrary scan line 55 in the object interior, and focusing only on photoacoustic waves generated on the scan line 55, it is found that a generation position Q of a photoacoustic wave 53 received by the ultrasound wave receiving element group 52 shifts, with the passage of time, from a near position on the scan line 55 to a distant position. Through modification of the delay time in the phasing delay circuit 8 in accordance with the reception time, therefore, the phasing delay circuit 8 can output, in the form of a signal of uniform phase, the photoacoustic wave signals generated at all points on one scan line 55.

This signal is exactly the same as a signal resulting from phasing delay of an echo signal obtained through transmission of an ultrasound wave beam in the direction of the scan line 55. Therefore, a photoacoustic signal intensity waveform can be calculated by resorting to the circuit configuration of FIG. 9 that is exactly the same as that of Example 1, for echo signal reception. A DCMP beamforming circuit 101 is a circuit that realizes the DCMP processing function of Example 1, and that outputs a modulation ratio γ. Therefore, a photoacoustic image of an entire surface in the object interior can be created through repeated irradiation of electromagnetic waves and reception of photoacoustic waves while the position of the scan line is shifted.

A configuration is also possible wherein there is provided a storage circuit 56 that stores reception signals, as in the figure, such that reception signals from an initial electromagnetic wave irradiation are stored in the storage circuit 56, and signals read out from the storage circuit 56 are used for second and subsequent reception signals. The reception signals by electromagnetic wave irradiation are the same every time, so long as the positions of the light source 51 and the ultrasound wave receiving element group 52 are not altered. Accordingly, the number of electromagnetic wave irradiations can be reduced, and a device having good efficiency can be achieved, by storing of reception signals from one single electromagnetic wave irradiation, and through repeated execution of processing of reading signals from the storage circuit 56 and calculating a reconstructed image on one scan line 55, while modifying the scan line position.

Thus, the present invention can also be used in an object information acquiring apparatus that receives photo-ultrasound waves generated as a result of irradiation of electromagnetic waves, and that reconstructs a photo-ultrasound image, and it becomes possible to provide a high-quality photo-ultrasound image.

In the present invention, a DCMP method has been explained as a specific example of adaptive beamforming, but APES (Amplitude and Phase Estimation) is a similar known method. In APES, the calculation method of the correlation matrix A upon calculation of the optimal weight vector W differs from Expression (2) in that the calculation method herein does not utilize sub-array signal vectors on their own, but difference vectors of the sub-array signal vectors and a mean vector thereof. Even accounting for the above difference, however, the characteristics of the method as an adaptive beamforming method are substantially identical to those of the DCMP method, and thus the present invention can be used in APES as well.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-183971, filed on Aug. 23, 2012, which is hereby incorporated by reference herein its entirety.

What is claimed is:

1. An object information acquiring apparatus comprising:
a plurality of receiving elements that receive an acoustic wave that has propagated from an object, and that convert the acoustic wave to an electric signal;
an adaptive beamformer that performs adaptive beamforming of adjusting reception directionality using the electric signal;

a delay-and-sum beamformer that performs delay-and-sum beamforming having preset directionality using the electric signal; and at least one CPU and memory, the at least one CPU and memory cooperating to function as an amplitude modulator that performs amplitude modulation of modulating an output signal of one of the adaptive beamformer and the delay-and-sum beamformer, using an output signal of the other one of the adaptive beamformer and the delay-and-sum beamformer, and the at least one CPU and memory cooperating to function as a generator that generates, on the basis of a signal outputted by the amplitude modulator, image data on the interior of the object.

2. The object information acquiring apparatus according to claim 1, wherein the CPU and memory perform amplitude modulation on an output signal from the delay-and-sum beamformer using an output signal from the adaptive beamformer.

3. The object information acquiring apparatus according to claim 2, further comprising:

a calculation circuit that calculates a modulation ratio on the basis of an output signal from the adaptive beamformer and signal intensity using a constraint vector, wherein the CPU and memory perform amplitude modulation on an output signal from the delay-and-sum beamformer by using the modulation ratio.

4. The object information acquiring apparatus according to claim 3, wherein the CPU and memory perform the amplitude modulation using the modulation ratio corrected using a mathematical function that changes over time.

5. The object information acquiring apparatus according to claim 4, wherein the CPU and memory correct the modulation ratio by using a monotonically increasing mathematical function.

6. The object information acquiring apparatus according to claim 4, wherein the CPU and memory correct the modulation ratio according to a linear interpolation formula that includes a parameter that changes over time.

7. The object information acquiring apparatus according to claim 1, wherein the CPU and memory perform amplitude modulation on an output signal from the adaptive beamformer by using an output signal from the delay-and-sum beamformer.

8. The object information acquiring apparatus according to claim 1, wherein the plurality of receiving elements is arrayed in one dimension, and generates the electric signal at respective positions, the adaptive beamformer and the delay-and-sum beamformer generate an output signal by performing beamforming on an electric signal at each of the positions, and the CPU and memory perform amplitude modulation at each of the positions, and the adaptive beanformer and the delay-and-sum beamformer beamform in a direction that intersects the direction of the arraying at a plurality of positions by using a signal generated and outputted by the CPU and memory.

9. The object information acquiring apparatus according to claim 1, wherein the adaptive beamforming is a Directionally Constrained Minimization of Power (DCMP) method.

10. The object information acquiring apparatus according to claim 1, further comprising:

a transmitting element that transmits an ultrasound wave to the object, wherein the plurality of receiving elements receive the acoustic wave that propagates from the object as a result of transmission of the ultrasound wave.

11. The object information acquiring apparatus according to claim 1, further comprising:

an irradiating element that irradiates an electromagnetic wave onto the object, wherein the plurality of receiving elements receive the acoustic wave that propagates from the object as a result of irradiation of the electromagnetic wave.

12. An information processing apparatus that generates image data on the interior of an object on the basis of an electric signal that is outputted by a plurality of receiving elements that receive an acoustic wave that propagates from the object, the information processing apparatus comprising:

an adaptive beamformer that performs adaptive beamforming of adjusting reception directionality using the electric signal;

a delay-and-sum beamformer that performs delay-and-sum beamforming having preset directionality using the electric signal; and at least one CPU and memory, the at least one CPU and memory cooperating to function as an amplitude modulator that performs amplitude modulation of modulating an output signal of one of the adaptive beamformer and the delay-and-sum beamformer, using an output signal of the other one of the adaptive beamformer and the delay-and-sum beamformer.

13. The information processing apparatus according to claim 12, wherein the CPU and memory perform amplitude modulation on an output signal from the delay-and-sum beamformer using an output signal from the adaptive beamformer.

14. The information processing apparatus according to claim 13, further comprising:

a calculation circuit that calculates a modulation ratio on the basis of an output signal from the adaptive beamformer and signal intensity using a constraint vector, wherein the CPU and memory perform amplitude modulation on an output signal from the delay-and-sum beamformer by using the modulation ratio.

15. The information processing apparatus according to claim 14, wherein the CPU and memory perform the amplitude modulation using the modulation ratio corrected using a mathematical function that changes over time.

16. The information processing apparatus according to claim 15, wherein the CPU and memory correct the modulation ratio by using a monotonically increasing mathematical function.

17. The information processing apparatus according to claim 15, wherein the CPU and memory correct the modulation ratio according to a linear interpolation formula that includes a parameter that changes over time.

18. The information processing apparatus according to claim 12, wherein the CPU and memory perform amplitude modulation on an output signal from the adaptive beamformer by using an output signal from the delay-and-sum beamformer.

19. The information processing apparatus according to claim 12, wherein the plurality of receiving elements is arrayed in one dimension, and generates the electric signal at respective positions, the adaptive beamformer and the delay-and-sum beamformer generate an output signal by performing beamforming on an electric signal at each of the positions, and the CPU and memory perform amplitude modulation at each of the positions, and the adaptive beamformer and the delay-and-sum beamformer beamform in a direction that intersects the direction of the arraying at a plurality of positions by using a signal generated and outputted by the CPU and memory.

20. The information processing apparatus according to claim 12, wherein the adaptive beamforming is a Directionally Constrained Minimization of Power (DCMP) method.

21. The information processing apparatus according to claim 12, further comprising:
a transmitting element that transmits an ultrasound wave to the object, wherein the plurality of receiving elements receive the acoustic wave that propagates from the object as a result of the ultrasound wave.

22. The information processing apparatus according to claim 12, further comprising:
an irradiating element that irradiates an electromagnetic wave onto the object,
wherein the plurality of receiving elements receive the acoustic wave that propagates from the object as a result of irradiation of the electromagnetic wave.

23. An object information acquiring method comprising:
a step of receiving, by a plurality of receiving elements, an acoustic wave that propagates from an object, and converting the acoustic wave to an electric signal;
an adaptive beamforming step of performing adaptive beamforming of adjusting reception directionality using the electric signal;
a delay-and-sum beamforming step of performing delay-and-sum beamforming having preset directionality using the electric signal;
an amplitude modulation step of performing amplitude modulation of modulating an output signal obtained in one of the adaptive beamforming step and the delay-and-sum beamforming step, using an output signal obtained in the other one of the adaptive beamforming step and the delay-and-sum beamforming step; and
a generation step of, on the basis of the amplitude-modulated signal, generating image data on the interior of the object.

24. The object information acquiring method according to claim 23, wherein the amplitude modulation step includes performing amplitude modulation on an output signal from the delay-and-sum beamforming step using an output signal from the adaptive beamforming step.

25. The object information acquiring method according to claim 24, further comprising:
a calculation step of calculating a modulation ratio on the basis of an output signal from the adaptive beamforming step and signal intensity using a constraint vector,
wherein the amplitude modulation step includes performing amplitude modulation on an output signal from the delay-and-sum beamforming step by using the modulation ratio.

26. The object information acquiring method according to claim 25, wherein the amplitude modulation step includes performing the amplitude modulation using the modulation ratio corrected using a mathematical function that changes over time.

27. The object information acquiring method according to claim 26, wherein the amplitude modulation step includes correcting the modulation ratio by using a monotonically increasing mathematical function.

28. The object information acquiring method according to claim 26, wherein the amplitude modulation step includes correcting the modulation ratio according to a linear interpolation formula that includes a parameter that changes over time.

29. The object information acquiring method according to claim 23, wherein the amplitude modulation step includes performing amplitude modulation on an output signal from the adaptive beamforming step by using an output signal from the delay-and-sum beamforming step.

30. The object information acquiring method according to claim 23, wherein the plurality of receiving elements is arrayed in one dimension, and generates the electric signal at respective positions,
the adaptive beamforming step and the delay-and-sum beamforming step together include generating an output signal by performing beamforming on an electric signal at each of the positions, and the amplitude modulation step includes performing amplitude modulation at each of the positions, and
the adaptive beamforming step and the delay-and-sum beamforming step beamform in a direction that intersects the direction of the arraying at a plurality of positions by using a signal generated and outputted in the amplitude modulation step.

31. The object information acquiring method according to claim 23, wherein the adaptive beamforming is a Directionally Constrained Minimization of Power (DCMP) method.

32. The object information acquiring method according to claim 23, wherein the acoustic wave that propagates from the object is an echo wave of an ultrasound wave that is transmitted to the object.

33. The object information acquiring method according to claim 23, wherein the acoustic wave that propagates from the object is a photoacoustic wave that is generated upon irradiation of the object with an electromagnetic wave.

* * * * *